United States Patent [19]

Fuse et al.

[11] Patent Number: 5,494,917
[45] Date of Patent: Feb. 27, 1996

[54] COGNITION ENHANCING QUINUCLIDINE COMPOUND

[75] Inventors: Yoshihide Fuse, Himeji; Kozo Yamamoto, Takasago; Hideyuki Kishida, Kakogawa; Toshiaki Miwa, Kobe; Takayoshi Hidaka, Kobe; Ikuo Katsumi, Kobe, all of Japan

[73] Assignee: Kanegafuchi Kagaku Kogyo Kabushiki Kaisha, Osaka, Japan

[21] Appl. No.: 313,118

[22] PCT Filed: Feb. 4, 1994

[86] PCT No.: PCT/JP94/00218

§ 371 Date: Oct. 12, 1994

§ 102(e) Date: Oct. 12, 1994

[87] PCT Pub. No.: WO94/19348

PCT Pub. Date: Sep. 1, 1994

[30] Foreign Application Priority Data

Feb. 17, 1993 [JP] Japan .................... 5-028281

[51] Int. Cl.[6] .................... A61K 31/44; C07D 211/72
[52] U.S. Cl. .................... 514/305; 546/133
[58] Field of Search ............... 546/133; 514/305

[56] References Cited

U.S. PATENT DOCUMENTS 4,853,376  8/1989  King ........................ 514/161
4,855,290  8/1989  Fisher et al. ................ 514/278

FOREIGN PATENT DOCUMENTS

| 0414394 | 2/1991 | European Pat. Off. . |
| 56-8381 | 1/1981 | Japan . |
| 61-280497 | 12/1986 | Japan . |
| 62-116580 | 5/1987 | Japan . |

OTHER PUBLICATIONS

Mikhlina, et al. "3-quinuclidinyl-diarylcarbinols" Khim. Geterotsikl. Soedin. 1976 (7) 935–9.

*Primary Examiner*—Richard D. Lovering
*Assistant Examiner*—Catherine Kilby Scalzo
*Attorney, Agent, or Firm*—Armstrong, Westerman, Hattori, McLeland & Naughton

[57] ABSTRACT

A cognition enhancer comprising, as an effective ingredient, a bicyclic compound containing nitrogen atom having the general formula (I):

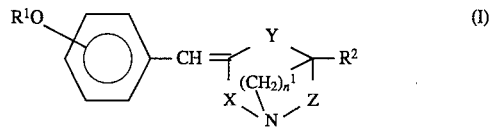

or a physiologically acceptable salt thereof.

2 Claims, No Drawings

COGNITION ENHANCING QUINUCLIDINE COMPOUND

TECHNICAL FIELD

The present invention relates to a novel bicyclic compound containing nitrogen atom and a physiologically acceptable salt thereof, which has cognition enhancing activity, and a cognition enhancer comprising the same as an effective ingredient.

BACKGROUND ART

With increasing a population of aged generation, dementia is occupying large weight in care of the aged. Although many medicines have been developed in order to improve various types of dementia such as dysmnesia, they are not fully enough in the points of efficacy, persistence and side effect.

For example, the function of cholinergic nervous system in hippocampus, amygdala and cerebral cortex is depressed in brains of patients of Alzheimer's disease (Pope et al., Trans. Am. Neurol. Assoc., 89, 15 (1964), Bowen et al., Brain, 266, 558 (1976) and Davies et al., Lancet, ii, 1043 (1976)). The above-mentioned is considered to be firmly concerned with nosogenesis of the impairment of memorization or memory which is main symptom of Alzheimer's disease (Whitehouse et al., Science, 215, 1237 (1982)). Therefore, there a possibility that these disturbances are improved by potentiating cholinergic nervous system. However, agonists of muscarinic cholinergic receptor which have been used up to date have high toxicity in spite of showing efficacy and therefore have not been practically used (Wettsein et al., Psychopharmacology, 84, 572 (1984) and Hollander et al., Biol. Psychiatry, 22, 1067 (1987)).

So, more effective and safe medicaments are required for the above-mentioned diseases.

As a result of continuous effort and detailed investigation of the present inventors in view of the above-mentioned actual circumstances, it has now been found that a novel bicyclic compound containing nitrogen atom and a salt thereof show anti-amnesic activity by oral administration in animal experiments such as experimental amnesic mice, that the above-mentioned compounds potentiate central cholinergic neural function as a characteristic of anti-amnesic activity by acting on muscarinic cholinergic receptors and that toxicity of the above-mentioned compounds is low. Therefore the above-mentioned compounds have been found to be useful as a cognition enhancer, and thus the present invention has been accomplished.

DISCLOSURE OF THE INVENTION

The present invention relates to a bicyclic compound containing nitrogen atom which has the general formula (I):

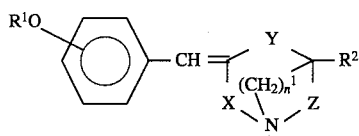

Wherein X is
a methylene chain of $-(CH_2)n^2-$ wherein $n^2$ is an integer of 0 to 4,
carbonyl group of

or
a group of

wherein $R^3$ is an alkyl group having 1 to 4 carbon atoms, phenyl group, benzyl group, hydroxyl group an alkoxyl group of $-OR^4$ wherein $R^4$ is an alkyl group having 1 or 3 carbon atoms, an ester group of $-CO_2R^5$ wherein $R_5$ is an alkyl group having 1 to 3 carbon atoms, or amino group, Y is
a methylene chain of $-(CH_2)n^3-$ wherein $n^3$ is an integer of 0 to 3,
carbonyl group of

or
a group of

Z is
a methylene chain of $-(CH_2)n^4-$ wherein $n^4$ is an integer of 0 to 3 or

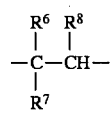

wherein $R^6$, $R^7$ and $R^8$ are independently an alkyl group having 1 to 4 carbon atoms, phenyl group, benzyl group, hydroxyl group, an alkoxyl group of $-OR^9$ wherein $R^9$ is an alkyl group having 1 to 3 carbon atoms, an ester group of $-CO_2R^{10}$ wherein $R^{10}$ is an alkyl group having 1 to 3 carbon atoms, or amino group, $R^1$ is hydrogen atom, an alkyl group having 1 to 4 carbon atoms, phenyl group, a substituted phenyl group or an acyl group of $R^{11}CO-$ wherein $R^{11}$ is an alkyl group having 1 to 3 carbon atoms, $R^2$ is hydrogen atom, an alkyl group having 1 to 4 carbon atoms, phenyl group, benzyl group, hydroxyl group, an alkoxyl group of $-OR^{12}$ wherein $R^{12}$ is an alkyl group having 1 to 3 carbon atoms, an ester group of $-CO_2R^{13}$ wherein $R^{13}$ is an alkyl group having 1 to 3 carbon atoms, or amino group, and $n^1$ is an integer of 1 to 5, provided that the number of carbon atoms contained in X, Y and Z, which carbon atoms are components of the ring including X, Y and Z, is at least 2, the number of carbon atoms contained in X, Y and $(CH_2)n^1$, which carbon atoms are components of the ring including X, Y and $(CH_2)n^1$, is at least 2, and the number of carbon atoms contained in Z and $(CH_2)n^1$, which carbon atoms are components of the ring including Z and $(CH_2)n^1$, is at least 3, or a physiologically acceptable salt thereof, and
a cognition enhancer comprising the same as an effective ingredient.

The compound of the present invention can be synthesized by, for instance, the following processes (1) to (8).

(1) The compound of the present invention can be obtained by reacting a compound having the general formula (II):

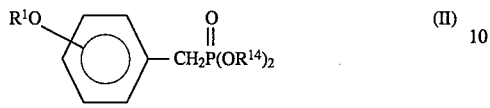

wherein $R^1$ is the same as defined above and $R^{14}$ is an alkyl group having 1 to 3 carbon atoms, or a compound having the general formula (III):

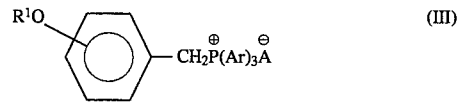

wherein Ar is an aryl group and A is a halogen atom, with a compound having the general formula (IV):

wherein X, Y, Z, $R^2$ and $n^1$ are the same as defined above, in the presence of a basic catalyst, for instance, a hydride of alkaline metal such as sodium hydride or potassium hydride, an alcoholate of alkaline metal such as sodium methylate or sodium ethylate, an amide of alkaline metal such as lithium diisopropylamide, an organic acid salt such as sodium acetate, a carbonate of alkaline metal such as sodium carbonate or potassium carbonate, a hydroxide of alkaline metal such as sodium hydroxide, an organic base such as piperidine and the like.

(2) The compound of the present invention can be obtained by reacting an aldehyde having the general formula (V):

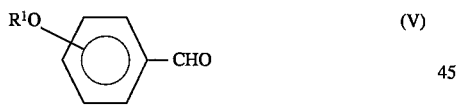

wherein $R^1$ is the same as defined above, with a compound having the general formula (VI):

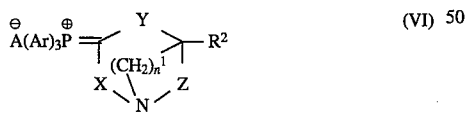

wherein X, Y, Z, $R^2$, $n^1$, Ar and A are the same as defined above, in the presence of a basic catalyst, for instance, a hydride of alkaline metal such as sodium hydride or potassium hydride, an alcoholate of alkaline metal such as sodium methylate or sodium ethylate, an amide of alkaline metal such as lithium diisopropylamide, an organic acid salt such as sodium acetate, a carbonate of alkaline metal such as sodium carbonate or potassium carbonate, a hydroxide of alkaline metal such as sodium hydroxide, an organic base such as piperidine and the like.

The above-mentioned synthesis processes (1) and (2) utilize the so-called Wittig reaction.

(3) The compound of the present invention can be obtained by reacting a compound having the general formula (VII):

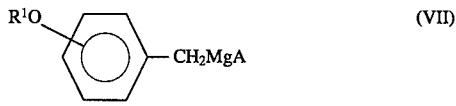

wherein $R^1$ and A are the same as defined above, with a compound having the general formula (IV):

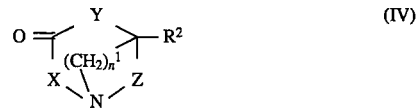

wherein X, Y, Z, $R^2$ and $n^1$ are the same as defined above, to obtain an alcohol having the general formula (VIII):

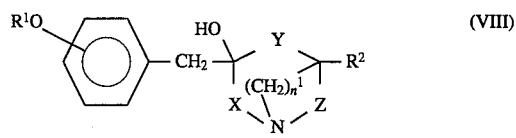

wherein X, Y, Z, $R^1$, $R^2$ and $n^1$ are the same as defined above, and followed by dehydrating the alcohol according to usual dehydration reaction of an alcohol.

As a catalyst used in the dehydration reaction, for instance, an organic acid such as sulfuric acid, boric acid, a hydrohalogenic acid, an organic sulfonic acid or oxalic acid, an acid salt such as potassium hydrogensulfate, alumina, thorium dioxide, thionyl chloride-pyridine, and the like, as well as various dehydrating agents can be used. Alternatively, the alcoholic hydroxyl group may be halogenated, sulfonated or esterified with a halogenating agent, a sulfonating agent or an esterifying agent, and thereafter eliminated according to elimination reaction to obtain the compound of the present invention.

(4) The compound of the present invention can be obtained by reacting an aldehyde having the general formula (V):

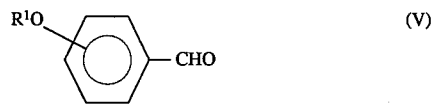

wherein $R^1$ is the same as defined above with a compound having the general formula (IX):

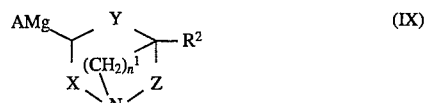

wherein X, Y, Z, $R^2$, $n^1$ and A are the same as defined above to obtain an alcohol having the general formula (X):

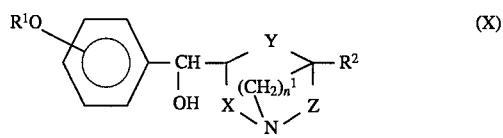

wherein X, Y, Z, $R^1$, $R^2$ and $n^1$ are the same as defined above, and followed by dehydrating the alcohol according to a usual dehydration reaction of an alcohol.

As a catalyst used in the dehydration reaction, for instance, an organic acid such as sulfuric acid, boric acid, a hydrohalogenic acid, an organic sulfonic acid or oxalic acid, an acid salt such as potassium hydrogensulfate, alumina, thorium dioxide, thionyl chloride-pyridine, and the like, and various dehydrating agents can be used. Alternatively, the alcoholic hydroxyl group may be halogenated, sulfonated or esterified with a halogenating agent, a sulfonating agent or an esterifying agent, and thereafter eliminated according to elimination reaction to obtain the compound of the present invention.

(5) A compound having the general formula (Ia) which is the compound (I) wherein X is carbonyl group:

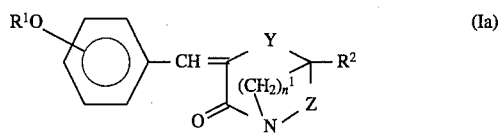

(Ia)

wherein Y, Z, $R^1$, $R^2$ and $n^1$ are the same as defined above, can be obtained by condensation of the aldehyde having the above-mentioned general formula (V) with a compound having the general formula (XI):

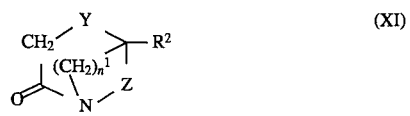

(XI)

wherein Y, Z, $R^2$ and $n^1$ are the same as defined above, without a catalyst or in the presence of an acid catalyst, for instance, a protonic acid such as sulfuric acid, benzenesulfonic acid or p-toluenesulfonic acid, a Lewis acid such as boron trifluoride and the like or in the presence of a basic catalyst, for instance, an organic base such as monoethanolamine or pyridine, a salt of organic acid such as sodium acetate, a hydroxide of alkaline such as potassium hydroxide, an amide of alkaline metal such as lithium diisopropylamide, an alcoholate of alkaline metal such as sodium methylate or sodium ethylate, a hydride of alkaline metal such as sodium hydride or potassium hydride and the like.

Further, the obtained compound (Ia) may be reduced according to a general reduction process of a carbonyl group of a carboxyamide, for instance, by using a reducing agent such as lithium aluminium hydride, to obtain a compound having the general formula (Ib) which is the compound (I) wherein X is methylene group:

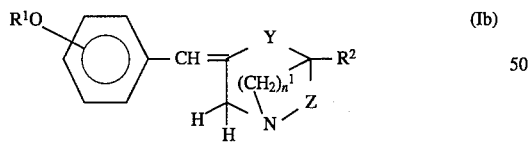

(Ib)

wherein Y, Z, $R^1$, $R^2$ and $n^1$ are the same as defined above.

(6) A compound having the general formula (Ic) which is the compound (I) wherein Y is carbonyl group:

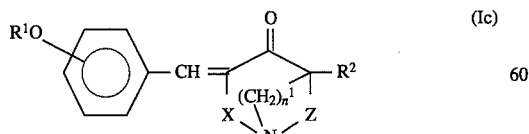

(Ic)

wherein X, Z, $R^1$, $R^2$ and $n^1$ are the same as defined above, can be obtained by condensation of the aldehyde having the above-mentioned general formula (V) with a compound having the general formula (XII):

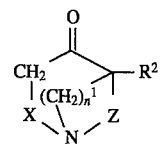

(XII)

wherein X, Z, $R^2$ and $n^1$ are the same as defined above, without a catalyst or in the presence of an acid catalyst, for instance, a protonic acid such as sulfuric acid, benzenesulfonic acid or p-toluenesulfonic acid, a Lewis acid such as boron trifluoride and the like or in the presence of a basic catalyst, for instance, an organic base such as monoethanolamine or pyridine, a salt of organic acid such as sodium acetate, a hydroxide of alkaline metal such as potassium hydroxide, an amide of alkaline metal such as lithium diisopropylamide, an alcoholate of alkaline metal such as sodium methylate or sodium ethylate, a hydride of alkaline metal such as sodium hydride or potassium hydride and the like.

Further, the obtained compound (Ic) may be reduced according to a general reduction process of a carbonyl group of a carboxyamide, for instance, by using a reducing agent such as lithium aluminium hydride, to obtain a compound having the general formula (Id) which is the compound (I) wherein Y is methylene group:

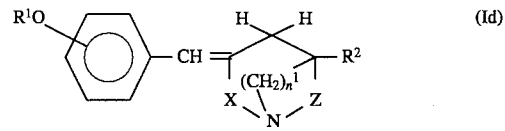

(Id)

wherein X, Z, $R^1$, $R^2$ and $n^1$ are the same as defined above.

(7) Among the compounds having the general formula (I), the compound having the above-mentioned general formula (Ia) can be obtained by reacting the aldehyde having the above-mentioned general formula (V) with a compound having the general formula (XIII):

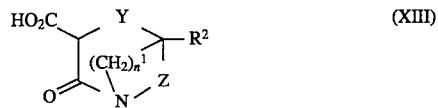

(XIII)

wherein Y, Z, $R^2$ and $n^1$ are the same as defined above, in the presence of a basic catalyst, for instance, an organic base such as pyrrolidine or piperidine, a hydride of alkaline metal such as lithium hydride or sodium hydride, a carbonate of alkaline metal such as sodium carbonate or potassium carbonate and the like. Thereafter, the compound (Ib) can be also obtained from the compound (Ia) in the same manner as in the process (5).

(8) Among the compounds having the general formula (I), the compound having the above-mentioned general formula (Ic) can be obtained by reacting the aldehyde having the above-mentioned general formula (V) with a compound having the general formula (XIV):

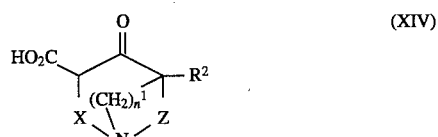

(XIV)

wherein X, Z, $R^2$ and $n^1$ are the same as defined above, in the presence of a basic catalyst, for instance, an organic base such as pyrrolidine or piperidine, a hydride of alkaline metal such as lithium or sodium hydride, a carbonate of alkaline metal such as sodium carbonate or potassium carbonate and the like. Thereafter, the compound (Id) can be also obtained from the compound (Ic) in the same manner as in the process (6).

In carrying out the above-mentioned reactions (1) to (8), in the case that starting material has hydroxyl group, amino group or carbonyl group, if necessary, functional groups thereof can be protected by introducing a protective group, and after the reaction, the protective group can be eliminated.

As the protective group, there can be used generally usable groups, for instance, trimethylsilyl group, tetrahydropyranyl group, butoxycarbonyl group, benzyloxycarbonyl group, ethylenedithio group and the like.

The compounds of the present invention obtained according to the above-mentioned processes can be used as a cognition enhancer.

BEST MODE FOR CARRYING OUT THE INVENTION

There are exemplified the representatives of the compounds of the present invention in Table 1.

When the above-mentioned salts are used as a cognition enhancer, pharmacologically acceptable salts are selected. A hydrochloride, a hydrobromide, a sulfate, an oxalate, a maleate or the like is preferable.

Physiological tests with the compound of the present invention are described below.

In order to examine effects as a cognition enhancer of the compound of the present invention, there were examined an anti-amnesic effect and a binding ability to M1 receptor.

These effects and acute toxicity were proved by the following tests.

As experimental animals, Wistar male rats and ddY male mice were used for the experiments after they were housed for a week under every 12 hours' dark-light cycle at room temperature of 24° to 26° C.

(1) Anti-amnesic effect

The effect on experimental amnesia in rat induced by lesioning basal forebrain (BF) was evaluated.

[Test method]

The experiment was carried out using an experimental apparatus of step-through type passive avoidance task for rat (made by Ohara-ika-sangyo K.K. ) comprising two compartments of dark and light. That is, the dark compartment

TABLE 1

| Compound No. | Structure | Molecular formula (Molecular weight) | m.p. (°C.) | Elemental analysis | | | | | |
|---|---|---|---|---|---|---|---|---|---|
| | | | | C | | H | | N | |
| | | | | Found | Cal. | Found | Cal. | Found | Cal. |
| 1a | cis compound | $C_{20}H_{21}NO$ (291.38) | 96 to 98 | 82.63 | 82.44 | 7.37 | 7.26 | 4.55 | 4.81 |
| 1b | trans compound | $C_{20}H_{21}NO$ (291.38) | 61 to 65 | 82.75 | 82.44 | 7.01 | 7.26 | 4.44 | 4.81 |

Cal: Calculation

The bicyclic compound containing nitrogen atom of the present invention can form a salt with an acid.

As the salt of the bicyclic compound containing nitrogen atom of the present invention, there are, for instance, (1) a salt with an organic acid such as formic acid, acetic acid, trichloroacetic acid, oxalic acid, maleic acid, tartaric acid, methanesulfonic acid, benzenesulfonic acid or toluenesulfonic acid, (2) a salt with an inorganic acid such as hydrochloric acid, hydrobromic acid, sulfuric acid or phosphoric acid, (3) a salt with an amino acid such as arginine, glutamic acid or ornithine.

(height: 200 cm, width: 150 cm, length: 200 cm) was a black plastic box and was floored with stainless grids for giving an electrical shock so that an electricity might be turned on a determined time after interception of a photobeam placed in the dark compartment. The light compartment made of transparent plastic (height: 200 cm, width: 250 cm, length: 200 cm) was provided adjacent to the dark compartment and was lightened from a location spaced 25 cm above by a 60 W electric lamp. Between the two compartments, there was provided an entrance with a guillotine door which could be opened and closed, and when the guillotine door was opened, a rat could freely move from one compartment to another.

Amnesia was induced by BF lesion. Among presently known methods for inducing amnesia, this method is considered to provide an animal model having the most similar pathology to Alzheimer's disease. The BF lesion was carried out by fixing an animal to a stereotaxic apparatus under nembutal anesthesia, inserting a stainless pipe into the BF area according to the brain map of Koenig, and injecting ibotenic acid bilaterally from the stainless pipe. In the sham-operation group, although craniotomy was carried out, ibotenic acid was not injected and therefore BF was not lesioned. The animals were used for experiments after recovery period of about 4 weeks.

Anti-amnesic effect was evaluated according to the following procedure.

A Wistar male rat (9 week-old) previously conditioned in the dark-light box was put in the light compartment and the guillotine door was opened. When the rat moved into the dark compartment, 150 V electrical shock was given for 3 seconds from the floor grid (aquisition trial). After 24 hours, retention trial was carried out in the same manner as in the aquisition trial, and latency, a period until the animal put in the light compartment entered the dark compartment, was measured maximally 300 seconds.

As positive controls, there were used AF102B (general name cis-2-methylspiro(1,3-oxathiolane-5,3') quinuclidine, available from Snow Brand Milk Products Co., Ltd.) which was M1 receptor agonist and tacrine (THA: tetrahydroaminoacridine) which was a cholinesterase inhibitor. Every test compound was suspended in a distilled water containing 2.5% of gum arabic and 0.2% of Tween 80. Compounds 1a and 1b were orally administered 1 hour before the aquisition trial and AF102B and tacrine were orally administered 30 minutes before the aquisition trial, respectively. The doses were 0.01 to 10 mg/kg.

[Test results]

The effect on the amnesia induced by BF lesion was shown in Table 2. Table 2 shows that, as the latency is longer, the anti-amnesic activity of the compound is more remarkable. Contrary to the sham-operation group wherein BF was not lesioned, in the control group wherein BF was lesioned the latency was notably shortened and therefrom it is recognized that amnesia was induced. On the other hand, in each group administered with a medicinal compound, there was observed antagonistic action to extend the latency.

The action pattern was so-called bell shape pattern wherein the activity was decreased both under a lower concentration and a higher concentration which pattern was often observed in case of using a cognition enhancer. The most potent minimal effective doses were 0.1 mg/kg in case of using Compound 1b, and 1 mg/kg in case of using Compound 1a and AF102B.

From the above-mentioned results, it is recognized that the compound of the present invention having the general formula (I) has a potent anti-amnesic activity in the animal model of Alzheimer's disease. The compound Nos. correspond to the compound Nos. in Table 1.

TABLE 2

|  | Dose (mg/kg) | Amount of animals used | Latency (sec.) | Significant difference[1] |
| --- | --- | --- | --- | --- |
| Sham-operation group | — | 32 | 270 | P < 0.05 |
| Control group | — | 67 | 46 | — |
| 1a | 0.1 | 10 | 38 | NS[2] |
|  | 1.0 | 10 | 156 | P < 0.05 |
| 1b | 0.01 | 10 | 76 | NS[2] |

TABLE 2-continued

|  | Dose (mg/kg) | Amount of animals used | Latency (sec.) | Significant difference[1] |
| --- | --- | --- | --- | --- |
|  | 0.1 | 10 | 182 | P < 0.05 |
|  | 1.0 | 10 | 139 | NS[2] |
|  | 10 | 10 | 99 | NS[2] |
| AF102B | 0.1 | 10 | 76 | NS[2] |
|  | 1.0 | 10 | 154 | P < 0.05 |
|  | 10 | 5 | 78 | NS[2] |
| Tacrine | 1.0 | 10 | 79 | NS[2] |
|  | 5.0 | 11 | 188 | P < 0.05 |

[1] Significant difference was evaluated according to Mann-Whitney test (P < 0.05) based on the control group.
[2] NS: No significance (2) Receptor binding activity The binding ability of the test compounds to M1 receptor was determined according to a modification of the method of Watson et al. (Life Sci., 32, 3001 (1983)). Concretely, 100 volume (W/V) of 10 mM Na—K phosphate buffer (pH 7.4) was added to a cerebral cortex of a Wistar male rat, and after the homogenization with polytron, the homogenate was centrifuged and washed twice. To 1 ml of the test liquid which was prepared by re-suspending the resulting precipitate, were added 20 μl of ($^3$H)pirenzepine, M1 receptor specific antagonist, and 20 μl of a test medicinal compound. After the incubation at 25° C. for 60 minutes, the mixture was filtrated and washed with a glass filter, and an amount of ($^3$H)pirenzepine bound to the receptor was counted by means of a liquid scintillation counter.

The binding ability to M2 receptor was determined according to a modification of the method of Buckley et al. (Mol. Pharmacol., 35, 469 (1989)). Concretely, 10 volume (W/V) of 50 mM Tris-HCl buffer (pH 7.4) was added to rat's heart, and after the homogenization with polytron, the homogenate was centrifuged and washed twice at 500 g for 10 minutes. The resulting supernatant was centrifuged four times at 40,000 g for 20 minutes. To 450 μl of the test liquid which was prepared by re-suspending the resulting precipitate, were added 200 μl of ($^3$H)N-methyl scopolamine, a muscarinic specific antagonist, and 100 μl of a test medicinal compound. After the incubation at 22° C. for 90 minutes, the amount of ($^3$H)N-methyl scopolamine found was determined.

The results are shown in Table 3.

TABLE 3

(Unit: nM)

| Compound No. | Receptor | IC$_{50}$ | Ki | nH |
| --- | --- | --- | --- | --- |
| 1a | M1 | 221 ± 32 | 152 ± 22 | 0.9 ± 0.06 |
|  | M2 | >10000 | — | — |
| 1b | M1 | 23 ± 3 | 16 ± 2 | 0.8 ± 0.07 |
|  | M2 | 4400 ± 100 | 1700 ± 40 | 1.0 ± 0.02 |
| AF102B | M1 | 729 ± 116 | 509 ± 80 | 0.8 ± 0.01 |
|  | M2 | >10000 | — | — |
| McN-A-343 | M1 | 842 ± 88 | 581 ± 61 | 0.9 ± 0.05 |
|  | M2 | >10000 | — | — |

In the above, IC$_{50}$ is a concentration of a medicinal compound when 50% of the binding of the receptor (M1, M2) and a radioactive ligand (($^3$H) pirenzepine, ($^3$H)N-methyl scopolamine) was inhibited. Ki is an affinity of a medicinal compound for a receptor, which is calculated from the following formula:

$$Ki = \frac{IC_{50}}{1 + \frac{C}{Kd}}$$

Ki: Affinity of a medicinal compound for a receptor $IC_{50}$: Concentration of a medicinal compound when 50% of a binding of a receptor and a radioactive ligand is inhibited, which concentration was calculated from a displacement curve C: Concentration of a radioactive ligand used in preparing the displacement curve Kd: Affinity of a radioactive ligand for a receptor which was calculated by Scatchard analysis In addition, nH is pseudo Hill coefficient which represents the number of a binding part of a receptor. When the values of $IC_{50}$ and Ki are smaller, a binding ability of a medicinal compound to a receptor is stronger.

Both Compounds 1a and 1b showed stronger binding ability to M1 than muscarinic agonists, AF102B (in course of clinical testing) and McN-A-343 (general name: 4[[(3-chlorophenyl) amino]carbonyl]oxy]-N, N, N-trimethyl-2-butyn-1-aminium chloride, available from McNeil Laboratories, spring House, Pa.). In the test of M2 receptor binding ability, although only Compound 1b showed $IC_{50}$ of not more than 10 μM among the test compounds, the binding ability was about 190 times weaker than M1 receptor binding ability. It has been proved that Compounds 1a and 1b have a strong and specific M1 receptor binding ability.

Muscarinic cholinergic receptors are now classified into three kinds of subtypes (M1, M2 and M3 ). Mainly, M1 is distributed in central nerve, M2 in heart and M3 in ganglion junction. Therefore drugs which stimulate M2 or M3 are likely to cause peripheral side effects such as cardiac depression or tremor. So selectivity toward M1 is preferable for the aim of potentiating central cholinergic nervous system.

That is, a muscarinic agonist having selectivity toward M1 receptor is considered to have an ability improving a disturbance of memory or perception in senile dementia.

As described above it has been proved that the compound of the present invention has the selective affinity for M1 receptor and therefore usable for the treatment of diseases due to an alteration of central nervous system, particularly diseases caused by a lowering of cholinergic function, such as Alzheimer's disease, senile dementia of Alzheimer's type, Huntington's chorea, Pick disease and tardive dyskinesia.

(3) Acute toxicity test

With respect to Compounds 1a and 1b shown in Table 1 as test compounds, the acute toxicity was examined using ddY mice according to the following method.

In each group, six male ddY mice weighing 27 to 30 g were employed. Compounds 1a and 1b suspended in an aqueous solution of 0.5% sodium carboxymethylcellulose were orally administered in a dose of 0.1 ml/10 g body weight. The general symptoms were observed for 2 weeks after the administration. The $LD_{50}$ (mg/kg) values were estimated from the ratio of the number of dead mice to the number of mice used.

As a result, there were observed no dead mice at a dose of 100 mg/kg with respect to Compounds 1a and 1b of the present invention. The $LD_{50}$ values of Compounds 1a and 1b were estimated to be not less than 100 mg/kg.

These results proved a low toxicity of the compounds of the present invention.

As the cognition enhancers of the present invention, there can be selected any pharmaceutical preparation which is administered orally, rectally or parenterally. Concrete examples of the pharmaceutical preparation are tablets, capsules, fine subtilaes, syrups, suppositories, ointments, injections, and the like.

As for excipients in the pharmaceutical preparation of the cognition enhancers of the present invention organic or inorganic pharmaceutical excipient material is employed in a solid or liquid state, which is usually inactive and suited for oral, rectal or parenteral administration. Concrete examples of such excipient are, for instance, crystalline cellulose, gelatin, lactose, starch, magnesium stearate, talc, vegetable or animal fat and oil, gum, polyalkyleneglycol, and the like. The compound of the present invention can be contained in an amount of 0.2 to 100 w/w % in the pharmaceutical preparation. The cognition enhancers of the present invention may contain other cognition enhancers or any other drugs, which are compatible with the agents of the present invention. In this case, the cognition enhancers of the present invention may not be the principal ingredients in the pharmaceutical preparation.

The cognition enhancers of the present invention are administered at a dose where the desired activity is generally achieved without any side effects.

Though a practical dose should be determined by a physician, the compounds of the present invention, as an active ingredient, is generally administered at a dose of 0.01 mg to 10 g, preferably about 0.1 mg to about 5 g, for an adult a day.

The cognition enhancers of the present invention can be administered as a pharmaceutical preparation which contains a unit dose of 0.001 mg to 5 g, preferably 0.1 mg to 1 g of the compounds as an effective ingredient.

The present invention is more specifically described and explained by means of the following Examples. The present invention is not limited to Examples.

EXAMPLE 1

Synthesis of cis form (1a) and trans form (1b) of Compound 1

Into 100 ml of 1,2-dimethoxyethane (DME) was suspended 3.0 g of 60% sodium hydride (oiliness). Thereto was added, at room temperature, a solution of 9.4 g of 3-quinuclidinone and 24 g of diethyl m-phenoxybenzilphosphonate which were dissolved in 100 ml of DME. The above-mentioned suspension was heated with stirring at 85° C. for 3 hours on an oil bath. The reaction suspension was cooled and diluted with an excess water, and then extracted three times with 100 ml of ethyl acetate. The extract was concentrated under reduced pressure. The residue was purified according to a column chromatography with silica gel as a carrier (eluting solvent: chloroform containing 1% of methanol) to give 11.0 g (yield: 50.5%) of the cis form (1a) of the disired Compound 1 and 4.6 g (yield: 21.1%) of the trans form (1b) of Compound 1.

(Compound 1a)

$^1$H-NMR spectrum (δ,CDCl$_3$): 1.77 (m, 4H), 2.45 (t, J=3Hz, 1H), 2.89 (m, 4H), 3.75 (s, 2H), 6.16 (t, J=2.5Hz, 1H), 6.81 to 7.37 (m, 9H)

$^{13}$C-NMR spectrum (δ, CDCl$_3$): 28.13, 34.07, 47.60, 55.89, 116.51, 118.62, 118.89, 120.21, 123.24, 123.33, 129.59, 129.74, 139.50, 147.62, 157.19, 157.30

(Compound 1b)

$^1$H-NMR spectrum (δ, CDCl$_3$): 1.68 (m, 4H), 2.91 (m, 4H), 3.01 (m, 1H), 3.56 (s, 2H), 6.19 (s, 1H), 6.90 to 7.39 (m, 9H)

$^{13}$C-NMR spectrum (δ, CDCl$_3$): 25.84, 27.05, 47.73, 56.58, 116.29, 118.58, 119.04, 119.31, 123.28, 129.42, 129.72, 139.17, 146.25, 157.09, 157.31

Pharmaceutical Preparation Example 1

A mixture of 100 g of Compound 1a, 55 g of lactose and 41 g of dry potato starch was kneaded with 20 ml of water. The mixture was extruded through 16 mesh screen and dried at 40° C. to give granule. Then the granule was mixed with 4 g of magnesium stearate uniformly and tabletted according to a usual method to give tablets containing 100 mg of Compound 1a per tablet (200 mg).

Pharmaceutical Preparation Example 2

The procedure of Pharmaceutical Preparation Example 1 was repeated except for using Compound 1b instead of Compound 1a in Pharmaceutical Preparation Example 1 to give tablets containing 100 mg of Compound 1b per tablet (200 mg).

Pharmaceutical Preparation Example 3

After 196 g of granule obtained in the same manner as in Pharmaceutical Preparation Example 1 was mixed with 4 g of magnesium stearate, each 200 mg of the mixture was filled into a hard capsule of size 2 to give a hard capsule containing 100 mg of Compound 1a per capsule.

Pharmaceutical Preparation Example 4

The procedure of Pharmaceutical Preparation Example 3 was repeated except for using Compound 1b instead of Compound 1a in Pharmaceutical Preparation Example 3 to give a hard capsule containing 100 mg of Compound 1b per capsule.

Pharmaceutical Preparation Example 5

| | |
|---|---|
| Compound 1a | 10.0 g |
| lactose | 84.0 g |
| crystalline cellulose | 4.5 g |
| magnesium stearate | 1.5 g |

The above-mentioned components were mixed enough to give powder containing 100 mg of Compound 1a per gram.

Pharmaceutical Preparation Example 6

The procedure of Pharmaceutical Preparation Example 5 was repeated except for using Compound 1b instead of Compound 1a in Pharmaceutical Preparation Example 5 to give powder containing 100 mg of Compound 1b per gram.

INDUSTRIAL APPLICABILITY

The bicyclic compound containing nitrogen atom of the present invention has a notable cognition enhancing activity and a toxicity thereof is low and therefore the bicyclic compound containing nitrogen atom is useful as cognition enhancer.

We claim:

1. A bicyclic nitrogen compound of the formula

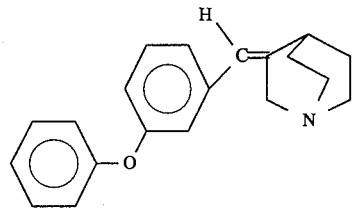

or

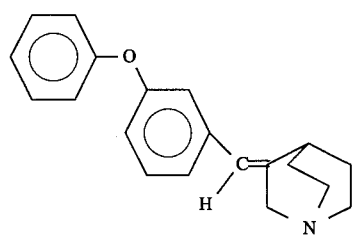

or a physiologically acceptable salt thereof.

2. A composition having cognition enhancing activity comprising the compound of claim 1, or a physiologically acceptable salt thereof, and a pharmaceutically acceptable carrier.

* * * * *